United States Patent [19]
White

[11] Patent Number: 5,269,812
[45] Date of Patent: * Dec. 14, 1993

[54] METHODS AND DEVICES EMPLOYED IN REPLACEMENT OF THE CORNEAL ENDOTHELIUM

[76] Inventor: Thomas C. White, 1127 Holly Dr., Sioux Falls, S. Dak. 57105

[*] Notice: The portion of the term of this patent subsequent to Aug. 18, 2009, has been disclaimed.

[21] Appl. No.: 886,376

[22] Filed: May 20, 1992

Related U.S. Application Data

[63] Continuation-in-part of Ser. No. 496,633, Mar. 21, 1990, Pat. No. 5,139,518, which is a continuation-in-part of Ser. No. 460,839, Jan. 23, 1990, Pat. No. 5,030,230, which is a continuation-in-part of Ser. No. 130,748, Dec. 9, 1987, Pat. No. 4,772,283, which is a continuation-in-part of Ser. No. 864,022, May 16, 1986, abandoned.

[51] Int. Cl.$^5$ .............................................. A61F 2/14
[52] U.S. Cl. ............................................ 623/5; 623/4
[58] Field of Search ...................... 623/4, 5; 606/166; 128/898

[56] References Cited

U.S. PATENT DOCUMENTS

| | | | |
|---|---|---|---|
| 4,077,411 | 3/1978 | Ward | 606/166 |
| 4,236,519 | 12/1980 | La Russa et al. | 606/166 |
| 4,842,599 | 6/1989 | Bronstein | 623/5 |
| 5,139,518 | 8/1992 | White | 623/5 |

OTHER PUBLICATIONS

Girard, *Corneal Surgery*, C. V. Mosby Company, 1981, pp. 162-165.

*Primary Examiner*—Randy C. Shay
*Attorney, Agent, or Firm*—Fredrikson & Byron

[57] ABSTRACT

The present invention provides a method of corneal transplantation and a corneal structure resulting from such transplants. According to this method, a thickness of a patient's cornea is removed to define a bore through the cornea, this thickness of corneal tissue defining a cap consisting of an outer thickness of tissue and a plug of an inner thickness of the tissue. An ocular implant sized and shaped similarly to the plug is then placed within the bore and surgically attached. The cap of the patient's own tissue is then placed in the bore and surgically reattached. The patient's cornea may be marked before removal of the tissue and this marking may be used to properly reorient the cap upon placing it in the bore for reattachment. The corneal structure of the invention includes an ocular implant sized to fit closely within a bore through a patient's cornea, the implant being attached to the cornea, and a cap formed from an outer thickness of the patient's cornea.

7 Claims, 4 Drawing Sheets

METHODS AND DEVICES EMPLOYED IN REPLACEMENT OF THE CORNEAL ENDOTHELIUM

RELATED APPLICATIONS

This application is a continuation-in part of co-pending U.S. patent application Ser. No. 496,633, filed Mar. 21, 1990, now U.S. Pat. No. 5,139,518 which is a continuation-in part of International application Ser. No. PCT/US88/03207, filed Sep. 19, 1988, and filed in the United States on Jan. 23, 1990 as Ser. No. 460,839, now U.S. Pat. No. 5,030,230, which is a continuation-in-part of U.S. patent application Ser. No. 130,748, filed Dec. 9, 1987, now U.S. Pat. No. 4,772,283, which in turn was a continuation in-part of U.S. patent application Ser. No. 864,022, filed May 16, 1986, now abandoned.

FIELD OF THE INVENTION

This invention relates to devices and methods for repairing and/or replacing damaged corneal tissue and particularly to such devices and methods as may be employed to replace damaged corneal endothelial tissue.

BACKGROUND OF THE INVENTION

For various reasons, the corneal portions of eyes must be surgically repaired or replaced. For example, the cornea may become scratched or scarred or otherwise physically damaged, greatly hindering sight. The cornea is also subject to the effects of various degenerative diseases, mandating replacement if the patient is to have normal or even near normal vision The cornea of the human eye is a specialized structure made up of substantially parallel, relatively compacted layers of tissue. The outermost or most superficial layer of the cornea is the epithelial layer. This is a protective layer of tissue which regenerates if injured. Moving inwardly in the eye is the base surface of the epithelial layer known as Bowman's membrane. Immediately adjacent the Bowman's membrane is the stroma of the cornea, which is an extra-cellular collagen architectural matrix with scattered keratocytic cells. The stroma layer is bounded at its deepest level by a cuticular, acellular membrane, referred to as Descemet's membrane, which is followed by a monolayer of single cell thickness of specialized endothelial cells which forms the posterior surface of the cornea. The endothelial layer does not regenerate and when it is diseased, scratched or otherwise injured, it must be replaced.

When disease or injury affect only the mid- or superficial stromal tissue and epithelial layer, as in certain scars, replacement of the superficial or a partial thickness of the anterior stroma may be sufficient to rehabilitate vision in the eye and a lamellar keroplasty or partial thickness transplant can be used. When, however, deep stroma and especially when the endothelium is diseased, those layers must be replaced and a full thickness or penetrating transplant is necessary.

A partial thickness transplant typically involves the replacement of a variable thickness of the outermost layers of the cornea but does not include replacement of the deep lining of Descemet's membrane and endothelial cell layer. The diseased tissue is replaced with an implant which may be a graft of tissue taken from the healthy cornea of a donor eye similar in size and shape to the tissue removed from the patient's cornea ("lamellar graft") or an artificial implant similar in size and shape to the tissue removed from the patient's cornea and made of a biologically acceptable material.

A full thickness transplant typically involves the replacement of all layers of the cornea, including the deep Descemet's membrane and the layer of endothelial cells. A cylindrical plug of the corneal tissue is replaced with a cylindrical implant which may be a plug of tissue cut from a donor cornea through the full thickness of corneal tissue ("penetrating graft") or an artificial implant sized and shaped to fit in a bore surgically formed through a patient's cornea.

The shape of the outermost surface of the cornea influences the quality of vision and changes made in the curvature of that surface can result in regular or irregular astigmatism or a change in the refractive state of the eye. Therefore, it would be desirable to be able to replace the deepest corneal layers without having to replace healthy tissue on the outermost surface of the cornea and to minimize deformation of the outermost corneal surface when all layers of corneal tissue must be replaced.

Furthermore, in India and many other areas of the world there is a great need for lamellar donor tissue due to a variety of factors, such as a higher incidence of superficial eye injuries and trauma to the stroma due to infections and the like; there generally is not as great a need for endothelial transplantation in these areas. Conversely, in the U.S. and other industrialized nations, the eye care tends to be better and the need for endothelial tissue can be significantly greater than the need for lamellar transplants. Furthermore, while supply of donor corneas is generally sufficient to meet demand in industrialized nations, in other countries the demand far outstrips supply. It would obviously be helpful if countries with sufficient supply could deliver tissue to other, more needy areas. Unfortunately, though, corneal tissue generally cannot be preserved for extended periods of time because it cannot be frozen—although the stroma in the epithelial layer can generally be frozen, freezing tends to damage the endothelial cells.

SUMMARY OF THE INVENTION

This invention relates to prosthetic devices and methods employed in replacing cornea endothelial tissue that allows the diseased or damaged corneal endothelial tissue to be replaced without replacing the outer layers of the patient's cornea in a manner resulting in less deformation of the outermost surface of the cornea (i.e. less astigmatism) than occurs with current full thickness transplant techniques.

A method of the invention comprises the steps of removing a cap comprising a partial thickness of outer layers of corneal tissue from a patient's cornea, removing a plug of the remaining portion of the patient's cornea from the area in which the outer thickness of tissue was removed, the plug including Descemet's membrane and corneal endothelial cells, thereby forming a bore through the remaining portion of the patient's cornea, and placing in the bore an ocular implant sized and shaped to fit closely in the bore. The ocular implant fits into and covers the area of the cornea from which the tissue was removed so that the resulting shape of the outermost surface of the patient's cornea is substantially the same as its pre-transplant shape.

In a preferred embodiment, the ocular implant comprises a replacement plug sized and shaped to fit closely in the bore and a cap of outer layers of tissue removed from the patient's cornea, the outer layers including the epithelial cell layer, Bowman's membrane and a variable amount of the corneal stroma. In this embodiment, the method further comprises the steps of placing the replacement plug into the bore, attaching the plug to the cornea, repositioning the cap in the area of the cornea from which the cap was removed and reattaching the cap to the cornea. The replacement plug may be made either of an artificial material or be obtained from the cornea of a healthy donor eye.

In order to ensure a proper fit of the patient's outer thickness within the bore, the method may additionally include marking the patient's cornea before removing the cap. When the cap is replaced in the bore, the mark may be used to properly orient the tissue to achieve an optimal fit.

Another embodiment of the invention comprises a method wherein a full thickness of the patient's cornea is removed to define a bore and the outer portion of this full thickness defines a cap of the patient's own tissue. A plug comprising a segment of a donor cornea or an ocular prosthesis is placed in the bore to replace an anterior portion of the patient's cornea and the patient's own cap is reattached. The method may also include the step of marking the patient's cornea before forming the bore to ensure proper orientation of the cap with respect to the rest of the cornea when it is reattached thereto.

BEST MODE FOR CARRYING OUT THE INVENTION

Figure 1:
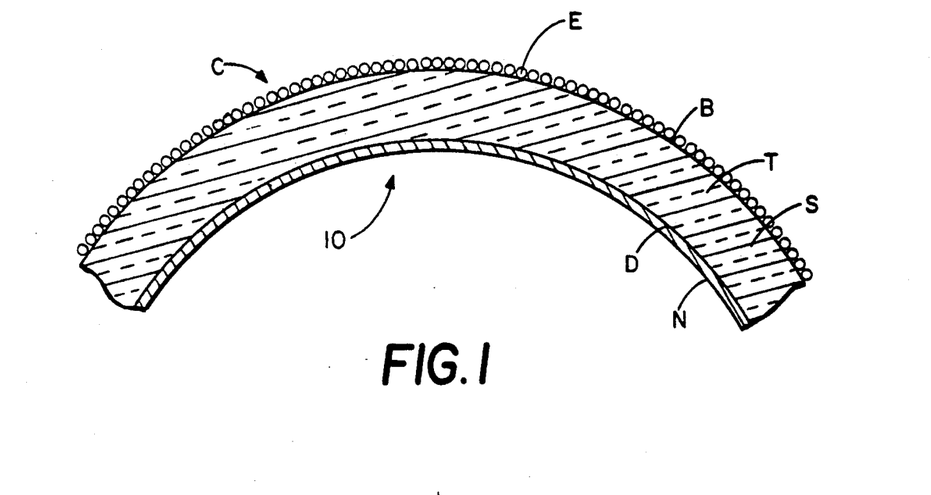
FIG. 1 is a partial cross-sectional view of the corneal-scleral rim of a human eye.

FIG. 1 is a partial cross-sectional view of the corneal-scleral rim of a human eye wherein the layers of the cornea C are shown diagrammatically. The outermost layer of the cornea, the epithelial layer, is shown as E. Moving inwardly in the cornea is the Bowman's membrane, shown as B. Immediately adjacent the Bowman's membrane is the stroma of the cornea, shown as T. The Descemet's membrane adjacent the stroma is shown as D, and the corneal endothelium is shown as N. The sclera is designated as S in the figure.

Figure 2:
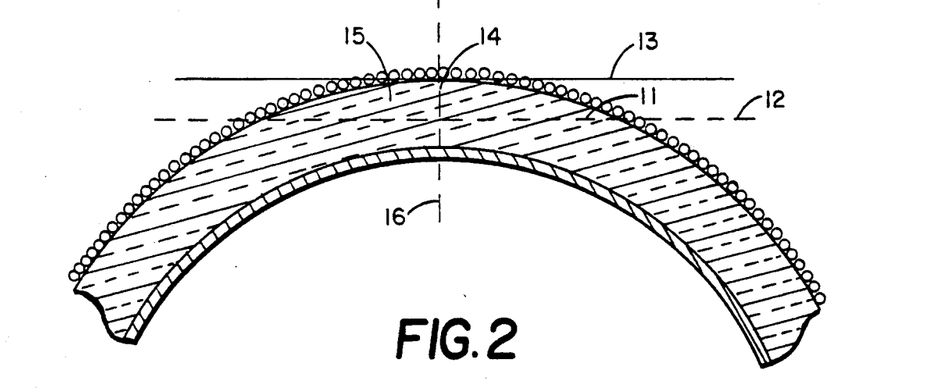
FIG. 2 is a partial cross-sectional view of the corneal scleral rim of a human eye.
Figure 3:
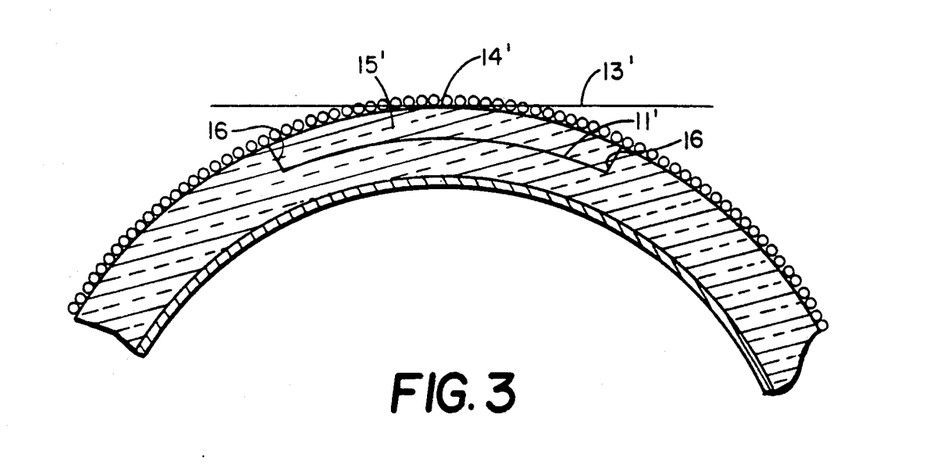
FIG. 3 is a partial cross-sectional view of the corneal-scleral rim of a human eye.

A donor replacement cap of corneal tissue from the cornea of a donor eye may be prepared using well known preparation techniques. Briefly, a donor globe must be cleaned and the outer layers of epithelial cells and stroma removed to a variable depth using a generally transverse cut. As shown in FIG. 2, the transverse cut 11 will desirably be made along an axis 12 that is generally parallel to a tangent 13 of the center 14 of the outermost surface of the thickness 15 of the cornea that is being removed. In a preferred embodiment, the tangent 13 will be generally perpendicular to the axis of vision 16. The transverse cut may be made flat as shown in FIG. 2 or it may be curved as shown in FIG. 3. To obtain a curved cut the surgeon may cut into the eye a predetermined distance (cuts into cornea represented as 17) and then make a generally transverse cut 11' which is curved while still being generally parallel to the tangent 13' of the center 14' of the outermost surface of the thickness 15' of the cornea being removed.

Figure 4:
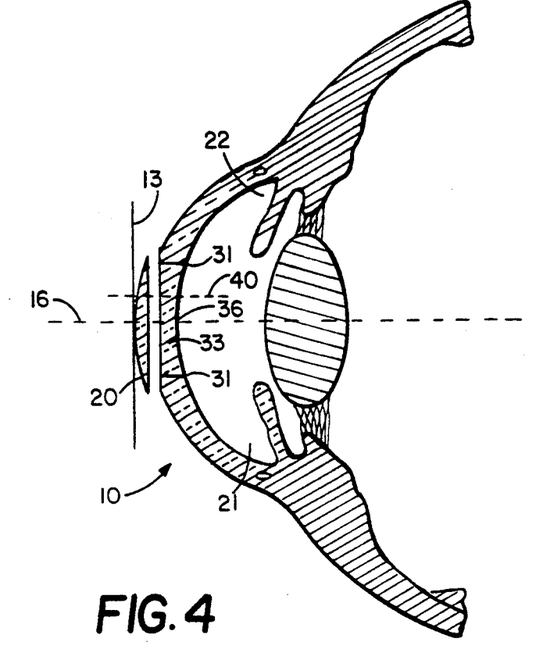
FIG. 4 is a cross-sectional view of the anterior portion of a human eye showing an excised portion of tissue.

Once the outer layers of corneal tissue have been removed, a corneal-scleral rim 10' is excised from the donor cornea, as shown in FIG. 4. (Line 21 represents the cuts made into the eye to excise the rim.) FIG. 4 shows a cross-sectional view of the front portion of a donor eye from which a cap 20 comprising a thickness of outer layers of tissue has been removed by a surgeon using a generally transverse cut. The excised portion of the cornea is placed in an appropriate preserving medium, such as tissue culture mediums, where it may be stored for a relatively short period of time, usually on the order of days or weeks. The donor cap removed from the donor eye with the transverse cut may also be preserved and used in a partial thickness transplant or as a donor cap in the transplantation method of this invention.

Figure 5:
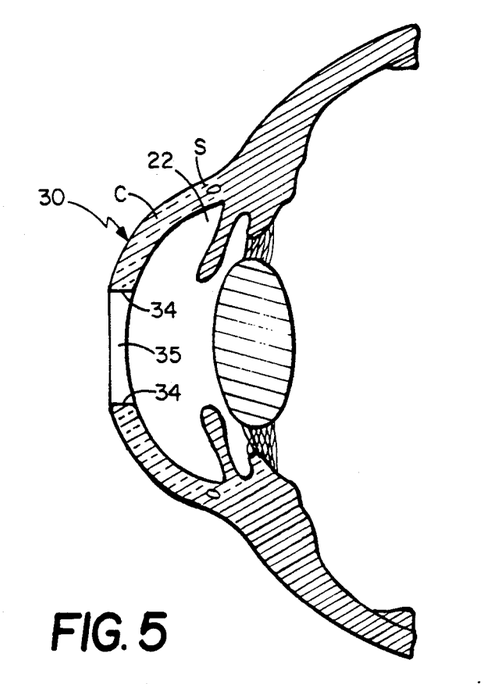
FIG. 5 is a cross-sectional view of the anterior portion of a human eye showing an excised portion of tissue.

During a corneal endothelium transplant of this invention, the patient-recipient cornea will be prepared by first removing a partial thickness of outer layers of corneal tissue. In the portion of the patient recipient's cornea remaining after the thickness has been removed, shown as 30 in FIG. 5, the surgeon cuts into the cornea (cuts represented as 31) and removes a plug 33 of diseased or damaged cornea comprising Descemet's membrane D and corneal endothelium N, the remaining corneal tissue rim 34 forming a bore 35 through the cornea.

Figure 6:
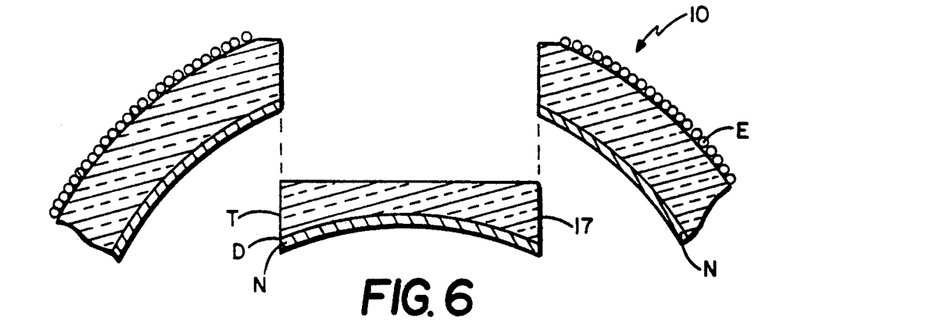
FIG 6 is a partial cross-sectional view of the corneal-scleral rim of a human eye showing an excised portion of tissue.

Upon completion of the removal of the patient's corneal plug 33, the corneal-scleral rim of the donor cornea, 10 in FIG. 6, is cut with the endothelial surface N up to form a donor replacement plug 17 comprising the posterior layers of the patient's cornea, the donor plug 17 having substantially the same dimensions as the corneal plug 33 being replaced.

As shown in FIG. 4 the cuts 31 made into the cornea to remove a plug of donor or patient corneal tissue will desirably be made along an axis 40 that is generally perpendicular to the tangent line 13 through the center of the outermost surface of the cornea, the tangent being substantially perpendicular to the line of vision 16. In a preferred embodiment, the plug of corneal patient tissue 33 will be removed from the center 36 of the area of cornea remaining after the thickness of outer layers of tissue was removed. The donor and patient corneal plugs are desirably generally cylindrical.

The transverse dimensions of the thickness of outer layers of tissue removed from the patient's or donor's cornea will desirably be equal to or greater than the transverse dimensions of the donor or patient corneal plug. It is to be understood that the transverse dimensions of the thickness and plug may differ but preferably the transverse dimensions of the plug will be only slightly less than the transverse dimensions of the outer thickness, so that the plug's transverse dimensions will be in the range of 80%-90% of the transverse dimensions of the thickness of outer corneal layers.

After the patient plug has been removed, the donor replacement plug may then be transferred and inserted into position in the recipient patient's cornea and secured in place by well known techniques, preferably with direct sutures. Once the posterior layers of the cornea have been replaced, then a replacement cap that is the partial thickness of outer layers of corneal tissue removed from the patient's cornea or a donor cap that is a similar thickness of outer layers of corneal tissue from a donor eye will be placed over the area of the patient's cornea from which the thickness of tissue was removed and over the replacement plug and secured in place with known attachment means, preferably with direct sutures.

Figure 7:
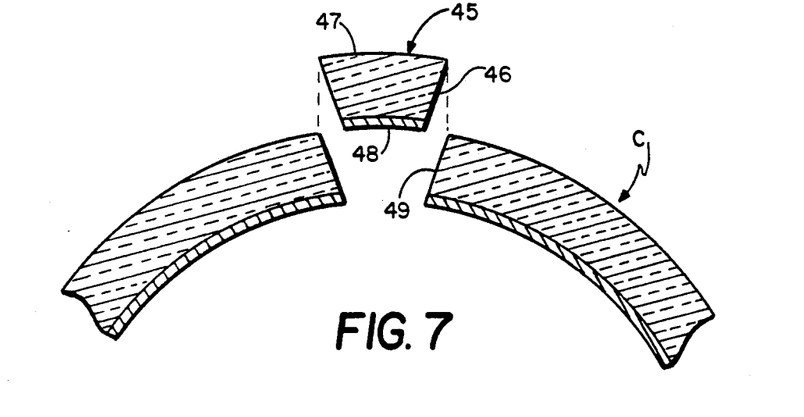
FIG. 7 is a partial cross-sectional view of the corneal-scleral rim of a human eye.

Referring to FIG. 7, another method of the invention is shown which comprises the steps of cutting through the full thickness of a patient's cornea C to form a plug 45 having a beveled edge 46 and an inner and outer surface 47, 48 and wherein the beveled edge slopes inwardly toward the center of the cornea from the outer surface to the inner surface, removing the plug to from the cornea thereby forming a bore 49 through the remaining portion of the patient's cornea, and placing into the bore an ocular implant (not shown) sized and shaped to fit closely in the bore.

Any suitable instrument can be employed in making the cuts into the cornea, such as a trephine of the type normally used in full thickness transplant procedures, a knife, motorized slicer, or laser. Similarly, any suitable instruments can be employed in making a transverse cut, such as a knife, motorized slicer, or laser.

The ocular implant used with a method of the invention may comprise fresh or preserved tissue or artificial tissue material either synthesized or derived from a biological source.

Figure 8:
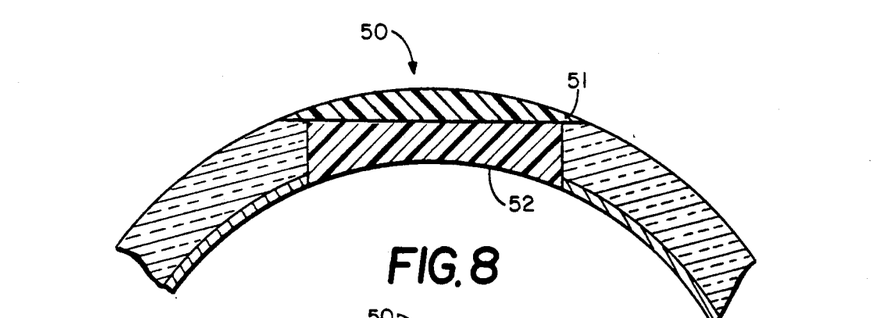
FIG. 8 is a cross-sectional view of a cornea showing a modified embodiment of the prosthesis of the invention implanted.
Figure 9:
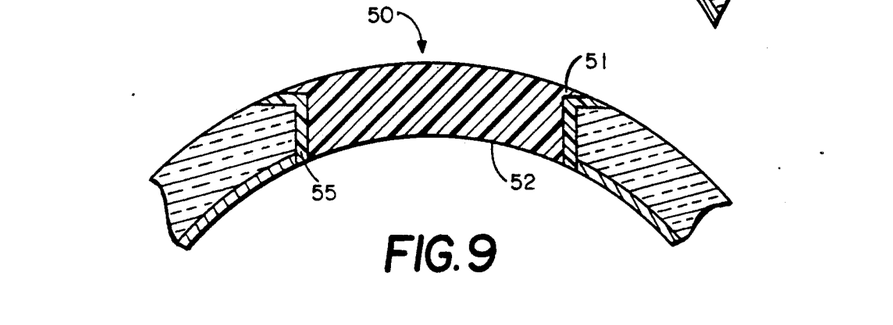
FIG. 9 is a cross-sectional view of a cornea showing a modified embodiment of the prosthesis of the invention implanted.

The invention also relates to an ocular prosthesis shown in FIG. 8 implanted in a cornea. The ocular prosthesis 50 comprises a replacement cap component 51 having a slightly domed anterior surface, the component being sized and configured to replace a partial thickness anterior portion of a cornea of an eye, the thickness being replaced including epithelial layer, Bowman's membrane and corneal stroma and a replacement plug component 52 extending posteriorly from the posterior surface of the anterior portion, sized and configured to replace a full thickness portion of the cornea, the plug component having a width or diameter smaller than the width or diameter of the cap component. The prosthesis may be formed as an integral unit or the two components may be attached to each other using any known attachment means such as adhesives and the like.

The prosthesis will desirably be of a material that can be sized and configured to fit the dimensions of the corneal tissue to be removed from a patient's cornea either before surgery or by the surgeon after the patient's tissue has been removed. Artificial materials which may be used in manufacturing a prosthesis of this invention or components thereof include but are not limited to biologically derived and processed materials and synthesized materials.

"Biologically derived and processed" as those terms are used in this description means that the material has been taken from a biological source and processed in such a way that its macroscopic structure has been altered from its naturally occurring state. An example of a biologically derived and processed material is collagen which has been isolated and purified from porcine tissue. The isolated collagen may be identical on a molecular level to naturally occurring collegen but its macroscopic structure is altered by the isolation process so that the collagen no longer has a fibrous structure as is found in naturally occurring collagen. Synthesized materials may include synthetic polymers such as polymethyl methacrylate, polycabonates, HEMA, polysulfones, silicones and synthetic materials fabricated to resemble naturally occurring substances.

The ocular prosthesis of this invention may further include a carrier 55 attached thereto, the carrier comprising preserved denatured tissue adapted for attachment to an eye. The carrier is desirably constructed of preserved biological tissue. The tissue may be of any suitable material, including cornea, sclera, fascia or other connective tissues such as tendon, cartilage or bone. Corneal tissue is preferred for those embodiments which require the carrier 55 to be transparent. The tissue must be preserved in a fashion which generally maintains the structural integrity of the extra-cellular collagen architectural matrix. Such preservation processes include but are not necessarily limited to glycerin dehydration, alcohol preservation, gluteraldehyde preservation, and formalin preservation. Preferably the preservation process denatures the tissue, analogously to tanning of rawhide, resulting in a number of benefits as described below.

In a preferred method of preserving such tissue, biological tissue, such as sclera, is removed, cleaned, and placed into preservative such as gluteraldehyde or formalin, where it may be stored for a period of days, weeks, or even months. When desired, the tissue is removed from the preservative and, if not already in proper configuration, manufactured into the appropriate configuration. The tissue is then united with the ocular prosthesis as described herein, and the resulting prosthesis is placed in a preservative that is compatible with the prosthesis material such as formalin. It should be noted that some prosthesis materials, such as PMMA, are incompatible with alcohol, but are compatible with other preservatives such as formalin, which is therefore a particularly preferred preservative for storage of the manufactured prosthesis. Desirably the preservative denatures the tissue. Denaturing may alter the antigenicity of the tissue to reduce or eliminate rejection complications, and in certain circumstances may permit use of biological tissue from other species. Denaturing also may tend to inhibit vascularization, a particularly desirable effect if the tissue is cornea. In most instances, the tissue is stored at least about three days in the preservative before use.

Manufacture of tissue into the appropriate physical configurations can be accomplished by well known techniques including the use of microkeratomes and trephines. See, e.g., Kaufman, "The Correction of Aphakia," 89 *American Journal of Ophthalmology*, 1 (Jan. 1980); Leigh, "Treatment of Gross Corneal Opacification by Lamellar and Annular Lamellar Keratoplasty," 39 *Brit. J. Ophthal.* 641 (1955); Waring, *Refrac-* tive *Keratoplasty*, 31 Resident & Staff Physician, 25-34 (May, 1985).

The prosthesis 50 may be attached to the preserved tissue carrier 55 by any suitable means, including but not limited to any of a variety of biologically acceptable adhesives. Such adhesives must be characterized by their ability to form a liquid-tight bond between the material of the prosthesis 50 and the preserved tissue carrier 55. Among adhesives suitable for this purpose are various well known dental adhesives. In particular, applicant has used an adhesive sold by Johnson & Johnson under the product number 2748. This two part adhesive has successfully bonded both formalin and gluteraldehyde preserved tissue to a polymethyl methacrylate prosthesis.

A particularly preferred class of adhesives are the bioadhesive polyphenolic proteins, such as that derived from the mussel genus Mytilus. These adhesives are characterized by a very low aqueous dispersive effect probably due, at least in part, to the high amounts of hydroxyproline (Hyp) and 3,4-dihydroxyphenylalanine (Dopa) present in the proteins. These adhesives have very low solubility at neutral or slightly basic pH, and adhere to many substrates, including biological substrates, durably in the presence of water, apparently for many years. They are particularly preferred for their long term durability under wet/humid conditions, for their ability to be applied to a wet substrate, and for their ability to bond durably to collagenous substrates. Furthermore, as they are biologically derived adhesives, they are likely to be biologically compatible in most forms.

These bioadhesive proteins may be isolated from the phenol glands of mussels according to well known techniques, including those described in Waite and Tanzer, *Science*, 212, 1038 (May 21, 1981); and U.S. Pat. No. 4,496,397, "Process for Purifying and Stabilizing Catechol-Containing Proteins and Materials Obtained Thereby," J. Waite (Jan. 29, 1985).

Such polyphenolic proteins appear to be characterized by including repeating decapeptide units having the following chemical formula:

Such decapeptides may be prepared and isolated according to the methods reported in U.S. Pat. No. 4,687,740, "Decapeptides Produced From Bioadhesive Polyphenolic Proteins," J. Waite (Aug. 18, 1987). Furthermore, such decapeptides may be polymerized to form large polyphenolic molecules having up to 1000 such repeating units, the linking group being an amino acid, an oligopeptide or a bifunctional spacer, as set forth in U.S. Pat. No. 4,687,740. European Pat. Application No. 87105775, published Nov. 11, 1987 (EP 244688) reports preferred adhesive formulations prepared utilizing such polyphenolic proteins. The formulations include the decapeptide unit, either singly or in polymerized form, together with a crosslinking agent (such as mushroom tyrosinase) and additional optional additives such as surfactants (such as SDS) and filler (such as collagen). Other methods for manufacturing such polyphenolic proteins are described in European Pat. Application No. 87104853 (published as EP 242656, Oct. 28, 1987), and A.C. Jouanneau, "A New Bio-Adhesive: A Protein Extract of Mussels—Attempts to Produce This Adhesive from *Mytilus Edulis* by Genetic Engineering," Biofutur (41, 65-66) 1985 (French). From the foregoing, it is seen that such bioadhesive polyphenolic proteins may be obtained through isolating them from natural producers of the proteins (i.e., the mussels themselves), or by synthesizing or genetically engineering them through standard techniques. Furthermore, as the unique adhesive properties of these proteins are believed to result from the presence of Dopa and hydroxyproline, certain changes in the remaining molecular structure of the proteins, likely including some amino acid substitutions (probably other than the Dopa and Hyp units), are likely to be possible to control and/or select properties of the bioadhesive.

In the corneal endothelial tissue replacement procedure using a prosthesis of this invention the eye is immobilized and the corneal portion to be removed is excised as described above employing suitable instruments. Upon completion of the removal of the corneal tissue, the prosthesis of the invention is inserted into the bore defined by the rim of the cornea. During the procedure, where each X is either hydroxyl or hydrogen, and each R is either hydrogen or methyl.

the prosthesis is supported by a suitable handle or grip such as a small suction cup applied to the outer surface of the prosthesis 54. Desirably, small sutures are taken about the periphery of the carrier 55 and are passed through the cornea to anchor the carrier 55 in place. Alternatively or in addition, a suitable adhesive such as a bioadhesive polyphenolic protein may be applied to the mating surfaces to securely bond them. The generally tight fit between the carrier and the corneal tissue rim assures that no leakage of aqueous humor from the eye will occur. Post operative procedures are similar to those commonly employed in corneal transplant surgery.

The carrier 55 is easily sutured or adhesively bonded (as by utilizing the polyphenolic protein adhesives described above) to the cornea (C), as the carrier is quite durable. The interstices within the carrier's collagen matrix, which are not substantially affected by the preferred denaturization, permit host-tissue cells to migrate and grow therein, laying down new collagen which interdigitates to form a "living bond" between the carrier 55 and the cornea (C). The carrier 55 may be of any suitable radial thickness, desirably at least 1 mm to provide sufficient tissue for suturing, and preferably between about 1.5 mm and about 3 mm. As described below, however, the carrier 55 may be substantially larger.

Further, the invention relates to a method of surgically repairing the cornea of an eye, comprising the steps of removing at least a partial thickness of the eye wall, including corneal tissue; and attaching an ocular prosthesis having a transparent prosthesis of biologically acceptable material to the eye wall covering the area from which tissue was removed. The attachment step is accomplished by applying to the prosthesis or the cornea, or both, polymerizable adhesive polyphenolic protein such as the type derived from the mussel genus Mytilus, and then polymerizing the protein to form a permanent adhesive bond therebetween.

The use of the methods of corneal transplantation of this invention provide significant advantages over the corneal transplant procedures of the prior art.

When a partial full thickness transplant is performed using known transplantation techniques a cylindrical plug of all layers of cornea is typically removed from a patient's cornea by cutting into the corner from the outer surface to the posterior endothelial surface using a trephine. The surgeon then uses the same trephine to remove a cylindrical plug of donor tissue that is similar in size and shape to the removed plug from a corneal scleral rim excised from a healthy donor eye.

The endothelial cell layer of the cornea is very fragile and should not be touched during the transplantation procedure. In order to obtain a cylindrical plug of donor tissue from an excised corneal scleral rim, the surgeon must lay the rim on a cutting surface with the epithelial cell side contacting the cutting surface and cut into the tissue from the endothelial side. The cutting process results in the walls of the plug and the walls of the bore through the remaining tissue being slightly deformed by the cutting edge of the instrument.

Because the plug removed from the patient's cornea is cut from the epithelial cell side in and the plug replacing the patient's tissue is cut from the endothelial side out, when the donor plug is placed in the patient's cornea the fit is not exact; this is likely to result in the outer surface of the plug extending past the outer surface of the patient's cornea or falling short of the outer surface of the patient's cornea causing the outer surface of the cornea to be slightly deformed and resulting in regular and irregular astigmatism.

The transplantation method of this invention greatly reduces the occurrence of such regular and irregular astigmatism because the outer layers of the corneal surface of both the patient and donor eye are removed using a transverse cut so the deformation caused by cutting will be similar in both the posterior surface of the cap and the anterior surface of the patient's remaining cornea.

In one particularly preferred embodiment of the present invention, a donor plug or a suitable prosthesis is used to replace the endothelial layers of the patient's cornea while the patient's own outer layers are used as the cap. Although this method may not work for all situations which require corneal transplantation, if the outer layers of the patient's cornea are healthy and undamaged, this can prove to be quite advantageous. In this method, a bore is formed through the patient's cornea and the inner layers of the corneal tissue are replaced with a donor plug, as explained above. However, rather than utilizing the cap formed of a donor's tissue, the patient's own tissue is used as the cap and is simply reattached to the cornea from which it was removed.

Figure 10:
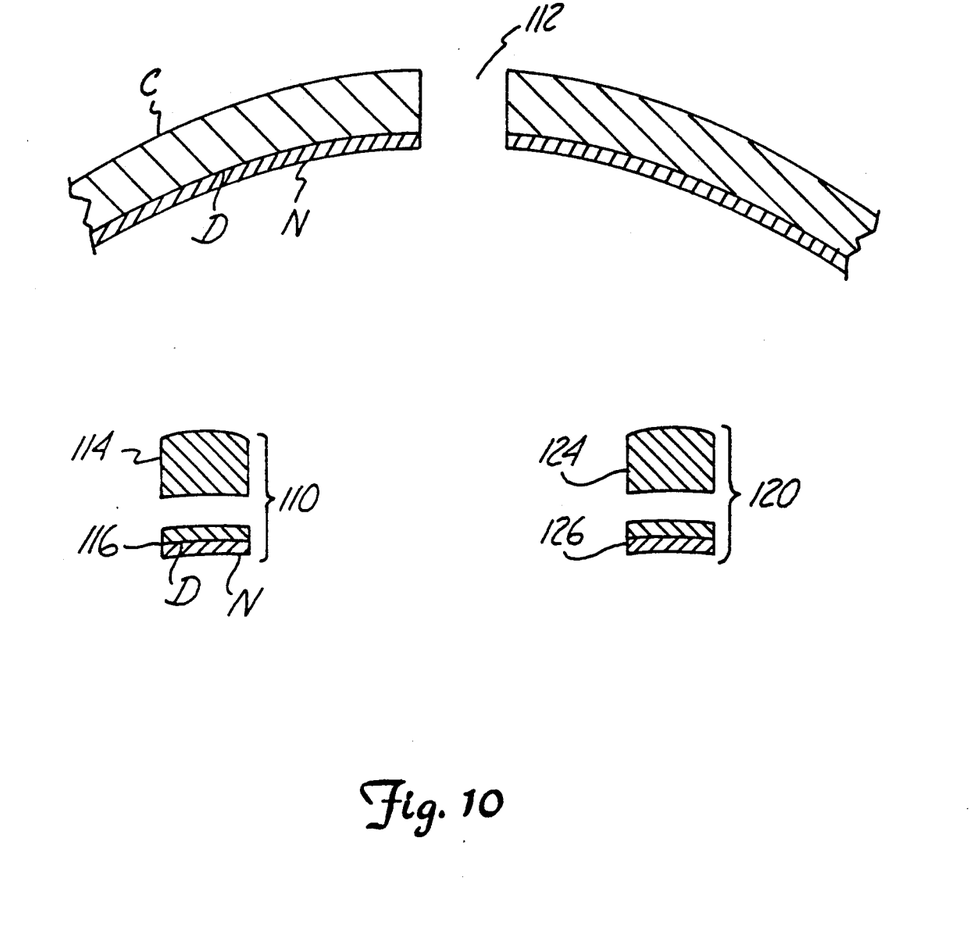
FIG. 10 is a cross-sectional view of a cornea having a bore formed therein, a full thickness of the patient's tissue, and a full thickness of donor tissue.

The cut which is made when forming the bore through the patient's eye can be made in any desirable fashion. One could use a transverse cut to form the cap, then perform a separate trephining operation to form the bore through the remaining portion of the patient's corneal tissue, as in the previous embodiment described above. However, it is to be understood that such a transverse cut is not necessary in the present embodiment of the invention. If so desired, one may instead form a bore through the entire thickness of the patient's cornea in a single cut, such as with a trephine or the like. Although it is generally desirable that the walls taper generally outwardly as shown in FIG. 7, the method of the present embodiment will perform its intended function even if a substantially cylindrical bore is formed through the cornea, as shown in FIG. 10.

If the bore through the patient's cornea is formed in a single cut, such as with a trephine, the cap can be formed after the bore is formed through the patient's cornea. As illustrated in FIG. 10, a full thickness 110 of corneal tissue having virtually any desired shape may be formed by cutting through the patient's cornea to define a bore 112 therein. The plug 110 may then be separated into a cap 114 and a plug 116. This may be accomplished by any known means, such as by cutting with a surgical knife or laser; this cut may be substantially perpendicular to the axis of vision, but may also be curvilinear, following the curve of the lamellae. In the embodiment described above, a generally transverse cut is used to form a cap and the plug of the patient's tissue is formed in a second cut. This will work equally as well with the present embodiment, particularly where the bore through the remaining thickness of the patient's cornea is sized and shaped to closely receive a portion of a trephined section of a donor cornea.

Once the bore 112 has been formed through the patient's cornea, a segment of donor tissue may be obtained as explained above. Although one will generally trephine through the entire donor cornea to define a full thickness 120 of corneal tissue, it is preferred that the full thickness be divided into a donor cap 124 and a donor plug 126. This can be accomplished by simply cutting a previously trephined full thickness 120 into two separate segments, or the plug 126 and the cap 124 may be cut from the donor eye in separate stages. The dimensions of the donor plug are desirably as close as possible to the dimensions of the patient's plug 116 which is being replaced. Once the donor tissue is cut to provide an appropriately sized donor plug, the donor plug may be implanted in the bore 112 through the patient's cornea by any suitable means, as explained more fully above. Unlike the previous embodiment, however, the patient's cap 114 is used rather than utilizing the donor's cap 124.

Alternatively, a suitable prosthetic plug (not shown) may be used instead of a plug 126 formed of tissue from a donor eye. Such a plug may be substantially the same as the replacement plug component 52 of the ocular prosthesis 50 described above in connection with FIG. 8. However, the ocular prosthesis used in the present embodiment would not include a replacement cap component 51; the patient's own tissue would instead be used as cap 114. Accordingly, the plug 116 of patient tissue should be substantially the same size as the prosthesis to ensure a good fit of the prosthesis within bore 112 and a length from the rearward surface of the prosthesis to the outer surface of the cap 114 substantially the same as that of the full thickness 110 removed from the patient's eye.

This invention has a number of advantages over the prior art. First, when the patient's own tissue is reattached rather than utilizing the donor's outer thickness, the amount of foreign tissue transplanted into the eye, i.e., the donor's tissue, is kept to a minimum. Since the amount of foreign tissue is significantly less than in a standard penetrating transplant, the antigenic load on the patient's eye, and hence the likelihood of rejection and failure of the transplant, is significantly less in the present invention. The blood vessels of the cornea are generally located in the outer layers of the cornea while the inner layers are less heavily populated with blood vessels. By utilizing the patient's own cap 114, the tissue coming into contact with the blood vessels will be the patient's own rather than foreign tissue from a donor. Because the cells of a patient's immune system which cause rejection of foreign tissue are carried in the bloodstream, by using a cap 114 formed of the patient's own corneal tissue, the corneal blood vessels will pass primarily through the patient's own tissue. The antigenic load of the donor tissue is therefore substantially reduced and the likelihood of rejection is relatively quite low.

One further advantage of the present embodiment of the invention is that utilization of the patient's own tissue in the outer layers of the cornea will ensure a better fit than simply using the donor's tissue. As explained above, the patient and donor corneas are generally trephined in opposite directions and this tends to cause discrepancies in the size and shape of the resulting bore 112 in the patient's eye and the full thickness 120 of the donor tissue. By using only a relatively small plug 126 of the donor's tissue which is positioned posteriorly in the cornea, the effects of these discrepancies upon the outermost surface of the cornea are minimized, thereby greatly reducing any astigmatism which may result from the discrepancies caused during trephining.

It has been found to be particularly useful to mark the patient's cornea before removing the full thickness 110 of corneal tissue from the patient's eye. A cornea generally does not comprise a perfect hemisphere, but rather the curvature of the outer surface of the cornea will vary at different positions on the cornea. Stated another way, a series of meridians drawn across the cornea will vary somewhat in their curvature. Thus, even though one simply replaces the patient's own cap 114, if the cap is not oriented in the same direction as when it was removed from the eye, the curvature of the outer surface of this cap may not match precisely with the curvature of the surrounding corneal tissue. In this sense, it is analogous to replacing the "lid" on a pumpkin—although the lid may fit reasonably well on the top of the pumpkin in any orientation, the lid will achieve its best fit when it is oriented in precisely the same direction in which it was removed.

By marking the patient's cornea before removing the tissue comprising the cap 114, one can ensure that the meridional orientation of the cap when it is replaced is the same as when it was removed. The cornea may be marked in any suitable manner. For instance, a small line may be drawn with an ink suitable for marking corneal tissue, as is known in the art, or a small scratch or other marking may be formed in the corneal tissue itself, which can regenerate to heal the scratch. The mark may comprise a generally straight line and desirably extends from a position located on the unaffected portion of the patient's cornea to a position located within the portion of corneal tissue to be removed to define the cap 114.

Once the thickness 110 of tissue is removed from the cornea and the donor plug 126 has been transplanted, the cap 116 may be replaced, making sure that the mark on the intact corneal tissue is substantially aligned with the mark on the cap 116. This ensures that the meridional orientation of the cap is substantially the same as when the cap was removed, providing a smooth, continuous outer surface for the cornea which is superior to that obtained without appropriately marking the cap 116.

The outer surface obtained by this method is vastly better than the match which would be obtained if a standard, full thickness transplant is used—the outer curvature of the patient's own tissue will tend to match much more closely than the outer curvature of a donor's tissue due to variations in corneal curvature between individuals and the location from which the donor tissue is removed. Since astigmatisms are caused by variations in the outer surface of the cornea, the method of the present invention can substantially reduce, and even virtually eliminate, astigmatisms due to the effects of these transplants.

One final advantage of the present invention is that the donor's healthy, undiseased cap 124 remains after the operation. As noted above, in many areas of the world there is a much higher need for outer layers of corneal tissue than for the inner layers. Because the epithelium and other portions of the inner layers of the eye generally cannot be frozen, it tends to be impractical for donor corneal tissue to be transported to more distant sites where the outer layers could be used. However, the stroma of a cornea can easily be frozen without detrimental effects. Because the donor's cap 124 comprises the outer thickness of the cornea, this tissue can be frozen and transported in an economical fashion to areas of the world where it can be used to replace diseased or damaged outer thicknesses of patient's eyes.

If so desired, the outer thickness of the entire donor cornea may be removed before forming the plug 126. At least a thin layer of stroma should be left when removing the outer thickness so that a plug 126 having a useful thickness and including stroma may be formed. This will ensure a supply of intact outer thicknesses of healthy donor tissue for storage and shipment; a lamellar graft of the desired size may be formed at the time of its transplantation rather than being limited to using a preformed donor cap 124.

The relative thicknesses of the cap 114 and the plugs 116, 126 may be varied as desired. The cap 114 should be thick enough to include at least the epithelium, Bowman's membrane and a portion of the stroma. It is generally preferred that the plug 116 be no more than about 50% as thick as the cap 114, with a thickness of no more than about 35% of the thickness of the cap being preferred and no more than about 25% being particularly preferred. (As noted above, it is desirable to have the patient's plug 116 and the donor's plug 126 of substantially the same dimension; accordingly, the ratios noted above between the cap 114 and the patient's plug 116 would be substantially the same as between the cap 114 and the donor plug 126).

Another advantage of the method of this invention is that because a thickness of outer layers of the cornea is removed from the patient's cornea, the front or back refractive surface of that thickness of the cornea can be altered to change the refractive state of the eye. This may be done by either the donor tissue processor or the surgical team.

It should be understood that the steps of the methods of this invention described herein may be separated over time and accomplished in stages, even including two or more surgical procedures. While a preferred embodiment of the present invention has been described, it should be understood that various changes, adaptations and modifications may be made therein without departing from the spirit of the invention and the scope of the appended claims.

What is claimed is:

1. Method of corneal transplantation comprising the steps of:
   (a) removing a full thickness of tissue from a patient's cornea to define a bore therein, the full thickness including a cap comprising a partial, outer thickness of tissue and a plug comprising a partial, inner thickness of tissue;
   (b) placing in said bore and surgically attaching to said cornea an ocular implant sized and shaped to have substantially the same dimensions as the plug of the patient's tissue; and
   (c) placing in said bore and surgically reattaching to said cornea the cap of the patient's tissue.

2. The method of claim 1 further comprising the step of marking the patient's cornea with a mark before removing the full thickness.

3. The method of claim 2 wherein the cornea is marked with a mark which extends from a position on said cap to a position on said cornea external of said cap to provide a means for establishing initial orientation of the cap with respect to the cornea.

4. The method of claim 3 further comprising the step of utilizing said mark to position said cap within said bore in approximately the same orientation with respect to the cornea as said initial orientation.

5. The method of claim 1 wherein the ocular implant comprises a donor plug including Desemet's membrane and corneal endothelium, further comprising the step of forming said donor plug from the cornea of a donor eye.

6. The method of claim 5 wherein the donor plug is formed to include a portion of the donor's stroma.

7. The method of claim 1 wherein the ocular implant comprises an ocular prosthesis, further comprising the step of forming said patient's plug to have dimensions substantially the same as those of the ocular prosthesis.

* * * * *